US008445439B2

(12) United States Patent
Tokura et al.

(10) Patent No.: US 8,445,439 B2
(45) Date of Patent: May 21, 2013

(54) ITCH SUPPRESSANT

(75) Inventors: Yoshiki Tokura, Fukuoka (JP); Shoko Fukamachi, Fukuoka (JP)

(73) Assignee: University of Occupational and Environmental Health, Japan, Fukuoka (JP)

( * ) Notice: Subject to any disclaimer, the term of this patent is extended or adjusted under 35 U.S.C. 154(b) by 0 days.

(21) Appl. No.: 13/503,153

(22) PCT Filed: Oct. 22, 2010

(86) PCT No.: PCT/JP2010/068695
§ 371 (c)(1),
(2), (4) Date: Apr. 20, 2012

(87) PCT Pub. No.: WO2011/049200
PCT Pub. Date: Apr. 28, 2011

(65) Prior Publication Data
US 2012/0214743 A1 Aug. 23, 2012

(30) Foreign Application Priority Data

Oct. 23, 2009 (JP) ................................. 2009-244528

(51) Int. Cl.
*A61K 38/00* (2006.01)
*A61P 17/00* (2006.01)
(52) U.S. Cl.
USPC ........................... 514/18.6; 514/5.3; 514/12.6
(58) Field of Classification Search
USPC ....................................................... 514/13.3
See application file for complete search history.

(56) References Cited

U.S. PATENT DOCUMENTS

| 2006/0177852 A1 | 8/2006 | Gabbai |
| 2008/0069869 A1* | 3/2008 | Rosenberg ..................... 424/450 |
| 2009/0232771 A1 | 9/2009 | Hinuma et al. |

FOREIGN PATENT DOCUMENTS

| JP | 2009-526754 | 7/2009 |
| WO | 2006/006722 | 1/2006 |

OTHER PUBLICATIONS

Hercogova J "Topical anti-itch therapy" Dermatologic Thearpy 18:341-343. Published Jul. 2005.*
Juanola et al "Mucosal mast cells are involved in CCK disruption of MMC in the rat intestine" Am J Physiol Gastrointest Liver Physiol 275:G63-G67. Published Jul. 1, 1998.*
International Search Report issued Nov. 22, 2010 in International (PCT) Application No. PCT/JP2010/068695, of which the present application is the national stage.
H. Nakagawa et al., "Tacrolimus ointment for atopic dermatitis", The Lancet, vol. 344, p. 883, Sep. 24, 1994.
N. Inagaki et al., "Evaluation of drugs for the treatment of atopic dermatitis in mice", Folia Pharmacologica Japonica, vol. 127, No. 2, pp. 109-115, 2006, with English summary.

Camp, R. D. R. et al., "Cyclosporin A in severe, therapy-resistant atopic dermatitis: report of an international workshop, Apr. 1993", British Journal of Dermatology, vol. 129, No. 2, pp. 217-220, 1993.
J. Hercogova, "Topical anti-itch therapy", Dermatologic Therapy, vol. 18, No. 4, p. 341-343, 2005.
S. Li et al., "CCK-8 Inhibits LPS-Induced IL-1β Production in Pulmonary Interstitial Macrophages by Modulating PKA, P38, and NF-$_K$B Pathway", Shock, vol. 27, No. 6, pp. 678-686, 2007.
A. Bozkurt et al., "Anti-inflammatory effects of leptin and cholecystokinin on acetic acid induced colitis in rats: role of capsaicin sensitive vagal afferent fibers", Regulatory Peptides, vol. 116, No. 1-3, pages109-118, 2003.
A.H. Meng et al., "Anti-inflammatory effect of cholecystokinin and its signal transduction mechanism in endotoxic shock rat", World Journal Gastroenterology, vol. 8, No. 4, pp. 712-717, 2002.
B. Cong et al., "Effect of cholecystokinin octapeptide on tumor necrosis factor α transcription and nuclear factor-$_K$B activity induced by lipopolysaccharide in rat pulmonary interstitial macrophages", World Journal of Gastroenterology, vol. 8, No. 4, pp. 718-723, 2002.
Y. Tokura, "Extrinsic and intrinsic types of atopic dermatitis", Journal of Dermatological Science 58, pp. 1-7, 2010.
C. Koga et al., "Possible Pathogenic Role of Th17 Cells for Atopic Dermatitis", Journal of Investigative Dermatology, vol. 128, pp. 2625-2630, 2008.
K. Hoffmann et al., "Gastrointestinal Hormones Cause Rapid c-Met Receptor Down-regulation by a Nobel Mechanism Involving Clathrin-mediated Endocytosis and a Lysosome-dependent Mechanism", The Journal of Biological Chemistry, vol. 281, No. 49, pp. 37705-37719, Dec. 8, 2006.

(Continued)

*Primary Examiner* — Cecilia J Tsang
*Assistant Examiner* — Zachary J Miknis
(74) *Attorney, Agent, or Firm* — Wenderoth, Lind & Ponack, L.L.P.

(57) ABSTRACT

The present invention provides an itch suppressant containing cholecystokinin 2 receptor agonist such as a peptide having an amino acid sequence homologous with a partial amino acid sequence of at least seven C-terminal amino acids of the peptide having the amino acid sequence represented by SEQ: ID No. 1 as an active ingredient as a rapid-acting itch suppressant effective in treating skin illnesses associated with strong itch such as atopic dermatitis having few side effects.

[SEQ: ID No. 1]
Val-Ser-Gln-Arg-Thr-Asp-Gly-Glu-Ser-Arg-Ala-His-
Leu-Gly-Ala-Leu-Leu-Ala-Arg-Tyr-Ile-Gln-Gln-Ala-
Arg-Lys-Ala-Pro-Ser-Gly-Arg-Met-Ser-Ile-Val-Lys-
Asn-Leu-Gln-Asn-Leu-Asp-Pro-Ser-His-Arg-Ile-Ser-
Asp-Arg-Asp-Tyr(SO$_3$H)-Met-Gly-Trp-Met-Asp-Phe-NH$_2$

3 Claims, 4 Drawing Sheets

OTHER PUBLICATIONS

L. Manni et al., "Cholecystokinin-8 enhances nerve growth factor synthesis and promotes recovery of capsaicin-induced sensory deficit", British Journal of Pharmacology, vol. 129, pp. 744-750, 2000.

K. Bhatia et al., "Effect of Penetration Enhancers and Iontophoresis on the Ultrastructure and Cholecystokinin-8 Permeability through Porcine Skin", Journal of Pharmaceutical Sciences, vol. 86, No. 9, pp. 1011-1015, 1997.

V. Srinivasan et al., "Iontophoresis of Polypeptides: Effect of Ethanol Pretreatment of Human Skin", Journal of Pharmaceutical Sciences, vol. 79, No. 7, pp. 588-591, 1990.

M. Korc et al., "Direct Modulation of Epidermal Growth Factor Binding by Cholecystokinin", Life Sciences, vol. 1. 33, pp. 561-568, 1983.

* cited by examiner

SEQUENCE LISTING

```
<160> NUMBER OF SEQ ID NOS: 26

<210> SEQ ID NO 1
<211> LENGTH: 58
<212> TYPE: PRT
<213> ORGANISM: Homo sapiens
<220> FEATURE:
<221> NAME/KEY: MISC_FEATURE
<222> LOCATION: (52)..(58)
<223> OTHER INFORMATION: Tyrosine at position 52 is O-sulfonated and
      phenylalanine at C-terminal is amidated.

<400> SEQUENCE: 1

Val Ser Gln Arg Thr Asp Gly Glu Ser Arg Ala His Leu Gly Ala Leu
1               5                   10                  15

Leu Ala Arg Tyr Ile Gln Gln Ala Arg Lys Ala Pro Ser Gly Arg Met
            20                  25                  30

Ser Ile Val Lys Asn Leu Gln Asn Leu Asp Pro Ser His Arg Ile Ser
        35                  40                  45

Asp Arg Asp Tyr Met Gly Trp Met Asp Phe
    50                  55

<210> SEQ ID NO 2
<211> LENGTH: 8
<212> TYPE: PRT
<213> ORGANISM: Artificial
<220> FEATURE:
<223> OTHER INFORMATION: Synthetic Construct, Tyrosine is O-sulfonated
      and phenylalanine at C-terminal is amidated.

<400> SEQUENCE: 2

Asp Tyr Met Gly Trp Met Asp Phe
1               5

<210> SEQ ID NO 3
<211> LENGTH: 7
<212> TYPE: PRT
<213> ORGANISM: artificial
<220> FEATURE:
<223> OTHER INFORMATION: Synthetic Construct, Tyrosine is O-sulfonated
      and phenylalanine at C-terminal is amidated.

<400> SEQUENCE: 3

Tyr Met Gly Trp Met Asp Phe
1               5
```

```
<210> SEQ ID NO 4
<211> LENGTH: 8
<212> TYPE: PRT
<213> ORGANISM: artificial
<220> FEATURE:
<223> OTHER INFORMATION: Synthetic Construct, Phenylalanine at
      C-terminal is amidated.

<400> SEQUENCE: 4

Asp Tyr Met Gly Trp Met Asp Phe
1               5

<210> SEQ ID NO 5
<211> LENGTH: 7
<212> TYPE: PRT
<213> ORGANISM: artificial
<220> FEATURE:
<223> OTHER INFORMATION: Synthetic Construct, Phenylalanine at
      C-terminal is amidated.

<400> SEQUENCE: 5

Tyr Met Gly Trp Met Asp Phe
1               5

<210> SEQ ID NO 6
<211> LENGTH: 6
<212> TYPE: PRT
<213> ORGANISM: artificial
<220> FEATURE:
<223> OTHER INFORMATION: Synthetic Construct, Phenylalanine at
      C-terminal is amidated.

<400> SEQUENCE: 6

Met Gly Trp Met Asp Phe
1               5

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gggaaatcgt gcgtgacatt                                               20

<210> SEQ ID NO 8
<211> LENGTH: 21
<212> TYPE: DNA
<213> ORGANISM: Artificial
<220> FEATURE:
<223> OTHER INFORMATION: Synthetic Construct

<400> SEQUENCE: 8
ggagttgaag gtagtttcgt g                                             21

<210> SEQ ID NO 9
<211> LENGTH: 21
<212> TYPE: DNA
<213> ORGANISM: Artificial
<220> FEATURE:
<223> OTHER INFORMATION: Synthetic Construct

<400> SEQUENCE: 9
gggacacgag aattggagct g                                             21

<210> SEQ ID NO 10
<211> LENGTH: 21
```

```
<212> TYPE: DNA
<213> ORGANISM: Artificial
<220> FEATURE:
<223> OTHER INFORMATION: Synthetic Construct

<400> SEQUENCE: 10
cggtgccaaa gatgaatgtg c                                              21

<210> SEQ ID NO 11
<211> LENGTH: 21
<212> TYPE: DNA
<213> ORGANISM: Artificial
<220> FEATURE:
<223> OTHER INFORMATION: Synthetic Construct

<400> SEQUENCE: 11
ctcagacctc tccccaaaca t                                              21

<210> SEQ ID NO 12
<211> LENGTH: 21
<212> TYPE: DNA
<213> ORGANISM: Artificial
<220> FEATURE:
<223> OTHER INFORMATION: Synthetic Construct

<400> SEQUENCE: 12
ccacaatgac cgtgtaggca g                                              21

<210> SEQ ID NO 13
<211> LENGTH: 20
<212> TYPE: DNA
<213> ORGANISM: Artificial
<220> FEATURE:
<223> OTHER INFORMATION: Synthetic Construct

<400> SEQUENCE: 13
gggaaatcgt gcgtgacatt                                                20

<210> SEQ ID NO 14
<211> LENGTH: 21
<212> TYPE: DNA
<213> ORGANISM: Artificial
<220> FEATURE:
<223> OTHER INFORMATION: Synthetic Construct

<400> SEQUENCE: 14
ggagttgaag gtagtttcgt g                                              21

<210> SEQ ID NO 15
<211> LENGTH: 20
<212> TYPE: DNA
<213> ORGANISM: Artificial
<220> FEATURE:
<223> OTHER INFORMATION: Synthetic Construct

<400> SEQUENCE: 15
gatggctgct acgtgcaact                                                20

<210> SEQ ID NO 16
<211> LENGTH: 19
<212> TYPE: DNA
<213> ORGANISM: Artificial
<220> FEATURE:
<223> OTHER INFORMATION: Synthetic Construct

<400> SEQUENCE: 16
cgcaccaccc gcttcttag                                                 19
```

<210> SEQ ID NO 17
<211> LENGTH: 19
<212> TYPE: DNA
<213> ORGANISM: Artificial
<220> FEATURE:
<223> OTHER INFORMATION: Synthetic Construct

<400> SEQUENCE: 17
cacgctggtt atcacggtg                                                    19

<210> SEQ ID NO 18
<211> LENGTH: 22
<212> TYPE: DNA
<213> ORGANISM: Artificial
<220> FEATURE:
<223> OTHER INFORMATION: Synthetic Construct

<400> SEQUENCE: 18
gcccatgaag taggtggtag tc                                                22

<210> SEQ ID NO 19
<211> LENGTH: 21
<212> TYPE: DNA
<213> ORGANISM: Artificial
<220> FEATURE:
<223> OTHER INFORMATION: Synthetic Construct

<400> SEQUENCE: 19
ctccaccaac acttctgagt c                                                 21

<210> SEQ ID NO 20
<211> LENGTH: 22
<212> TYPE: DNA
<213> ORGANISM: Artificial
<220> FEATURE:
<223> OTHER INFORMATION: Synthetic Construct

<400> SEQUENCE: 20
tcaccactgt attgaatgca gc                                                22

<210> SEQ ID NO 21
<211> LENGTH: 20
<212> TYPE: DNA
<213> ORGANISM: Artificial
<220> FEATURE:
<223> OTHER INFORMATION: Synthetic Construct

<400> SEQUENCE: 21
agccatgtac gtagccatcc                                                   20

<210> SEQ ID NO 22
<211> LENGTH: 21
<212> TYPE: DNA
<213> ORGANISM: Artificial
<220> FEATURE:
<223> OTHER INFORMATION: Synthetic Construct

<400> SEQUENCE: 22
ctctcagctg tggttggtga a                                                 21

<210> SEQ ID NO 23
<211> LENGTH: 20
<212> TYPE: DNA
<213> ORGANISM: Artificial
<220> FEATURE:
<223> OTHER INFORMATION: Synthetic Construct

```
<400> SEQUENCE: 23
tctcccgcga actctaccta                                           20

<210> SEQ ID NO 24
<211> LENGTH: 20
<212> TYPE: DNA
<213> ORGANISM: Artificial
<220> FEATURE:
<223> OTHER INFORMATION: Synthetic Construct

<400> SEQUENCE: 24
acacagcagc catcactgtc                                           20

<210> SEQ ID NO 25
<211> LENGTH: 20
<212> TYPE: DNA
<213> ORGANISM: Artificial
<220> FEATURE:
<223> OTHER INFORMATION: Synthetic Construct

<400> SEQUENCE: 25
tgggcaacgt agtggtgata                                           20

<210> SEQ ID NO 26
<211> LENGTH: 20
<212> TYPE: DNA
<213> ORGANISM: Artificial
<220> FEATURE:
<223> OTHER INFORMATION: Synthetic Construct

<400> SEQUENCE: 26
cacggctgtc atggagtaga                                           20
```

ITCH SUPPRESSANT

TECHNICAL FIELD

The present invention relates to an itch suppressant suppressing itch associated with skin illness.

BACKGROUND ART

Skin illnesses such as atopic dermatitis, contact dermatitis, urticaria and prurigo are often accompanied by itch (itch: an unpleasant feeling of skin making one fell like scratching). The itch causes not only a vicious cycle of exacerbation of pathology and increasing of the itch due to induced scratch behavior but also a lowered efficiency in daily life and job as well as sleep problem that leads to deterioration of Quality of Life (hereinafter QOL). Hence, the suppression of the itch is important in the treatment of skin illness along with the suppression of inflammation response in the skin.

Drugs containing various synthetic steroids are widely used for the treatment of skin illnesses and significant therapeutic effects have been achieved. However, steroid drugs for external use have no direct suppressing effect toward the itch and are considered to suppress the itch in an indirect manner by suppressing the inflammation response. Since the itch in atopic dermatitis and the like are considered to be the phenomenon arising from histamine from mast cells, antihistamine drugs and anti-allergic drugs are often administered as drugs for internal or external use.

In recent years, drugs for external use containing tacrolimus, an immune-suppressing drug have been used (for example, see Hidemi Nakagawa et al., "Tacrolimus ointment for atopic dermatitis", Lancet, Vol. 344 (1994), p. 883). Similarly to steroid drugs, the major mechanism of action of tacrolimus is suppression of inflammatory response and the suppression of the scratch behavior by tacrolimus is observed in the experiments using disease model mouse of atopic dermatitis (for example, see Naoki Inagaki and Hiroichi Nagai, "Evaluation of drugs for the treatment of atopic dermatitis in mice", Folia Pharmacologica Japonica, Vol. 127 (2006), No. 2, p. 109-115).

Recently, internal use of cyclosporin, an immune-suppressing drug, has been under consideration for patients with severe atopic dermatitis which cannot be controlled by traditional general therapies or for patients difficult to treat with steroids (for example, see Camp, R. D. et al., "Cyclosporin A in severe, therapy-resistant atopic dermatitis", report of an international workshop, April 1993, British Journal of Dermatology, Vol. 129, No. 2 (1993), p. 217-220). In Japan, the use of cyclosporin for patients with severe atopic dermatitis has been approved under certain conditions.

In other approaches, the methods and drugs that control itch or inflammatory response in gene level have been investigated. For example, WO 2006/006722 discloses a cell regeneration-, proliferation- and differentiation-controlling agent containing particular proteins comprising cholecystokinin, a neuropeptide or analogues thereof and a method for treating in which cell regeneration, proliferation and differentiation are involved such as obesity, diabetes, immune disorder, liver disorder, alimentary disorder, tissue damage in cosmetic surgery by administering such agent and a use of cholecystokinin as preventive and/or therapeutic agent for immune disorders such as atopic dermatitis.

Also, Japanese Unexamined Patent Application Publication (Translation of PCT Application) No. 2009-526754 discloses an invention relating to a pharmaceutical composition comprising at least one pharmaceutical agent as an active ingredient, nanostructures for facilitating intake in vivo and liquid and a therapeutic agent for itch using a neuropeptide.

PRIOR ART DOCUMENTS

Patent Documents

Patent Document 1: WO 2006/006722 (claims 26 and 34,)
Patent Document 2: Japanese Unexamined Patent Application Publication (Translation of PCT Application) No. 2009-526754 (paragraph 0052 to 0053)

Non-Patent Documents

Non-patent Document 1: Hidemi Nakagawa et al., "Tacrolimus ointment for atopic dermatitis", Lancet, Vol. 344 (1994), p. 883
Non-patent Document 2: Naoki Inagaki and Hiroichi Nagai, "Evaluation of drugs for the treatment of atopic dermatitis in mice", Folia Pharmacologica Japonica, Vol. 127 (2006), No. 2, p. 109-115
Non-patent Document 3: Camp, R. D. et al., "Cyclosporin A in severe, therapy-resistant atopic dermatitis", report of an international workshop, April 1993, British Journal of Dermatology, Vol. 129, No. 2 (1993), p. 217-220

SUMMARY OF THE INVENTION

Problems to be Solved by the Invention

However, since the steroid drugs and the tacrolimus drugs have a risk of severe side effects, prolonged use of these drugs and the use of them to children in whom the scratch behavior associated with the itch is largely responsible for the onset of the skin illnesses are limited.

In addition, the efficacy of the antihistamine drugs to the atopic dermatitis associated with strong itch is called in question because of their side effects such as sleepiness and dry mouth, differences in the effect between individuals, strong resistance of a part of the itch of the patients of atopic dermatitis against the antihistamine drugs and the like.

Moreover, the cyclosporin drugs for internal use have a risk of the side effect of kidney dysfunction, high blood pressure and the like associated with their prolonged use.

In Patent Documents 1 and 2, though applicability of the use as an itch suppressant is disclosed, there are no descriptions of any experimental examples, detailed active ingredients or effective amounts, or any effects.

The present invention has been achieved in view of the aforementioned problems and the object of the present invention is to provide a rapid-acting itch suppressant effective in treating skin illnesses associated with strong itch such as atopic dermatitis having few side effects.

Means for Solving the Problems

Through further study on the suppression of the itch mediated by cholecystokinin 2 receptor (CCK2R) signaling based on novel insight that CCK2R is highly expressed in normal human epidermal keratinocytes (NHEK) stimulated by substance P, an itch-inducing peptide, the present inventors succeeded in developing the present invention.

The present invention provides an itch suppressant containing cholecystokinin 2 receptor (CCK2R) agonist as an active ingredient.

Cholecystokinin, CCK is known as a gastrointestinal hormone as well as acts as a neuropeptide in the central nervous system. Among neuropeptides, CCK is most abundant in the central nervous system and known to involve in various physiologies such as anxiety, dysphoria, memory and diet behavior. Cholecystokinin is the generic name of peptides derived from similar gene product (preprocholecystokinin) having various amino acid lengths sharing C-terminal amino acid sequences, which are referred to as CCK58, CCK39, CCK33, CCK22, CCK8, CCK7 and the like based on their numbers of amino acid residues.

Little has been known about the function of cholecystokinin and its receptor in skin, however, it was found that stimulus of itch-inducing substance such as substance P leads to high expression of cholecystokinin 2 receptor (hereinafter may be abbreviated as "CCK2R") and an agonist directed to CCK2R thus expressed suppressed the scratch behavior in experimental animals.

In the itch suppressant according to the present invention, the cholecystokinin 2 receptor agonist is preferably one or more peptides selected from the group consisting of:

(1) a peptide having an amino acid sequence homologous with a partial amino acid sequence of at least seven C-terminal amino acids of the peptide having the amino acid sequence represented by SEQ ID NO: 1; and

[SEQ: ID No. 1]
Val-Ser-Gln-Arg-Thr-Asp-Gly-Glu-Ser-Arg-Ala-His-

Leu-Gly-Ala-Leu-Leu-Ala-Arg-Tyr-Ile-Gln-Gln-Ala-

Arg-Lys-Ala-Pro-Ser-Gly-Arg-Met-Ser-Ile-Val-Lys-

Asn-Leu-Gln-Asn-Leu-Asp-Pro-Ser-His-Arg-Ile-Ser-

Asp-Arg-Asp-Tyr(SO$_3$H)-Met-Gly-Trp-Met-Asp-Phe-NH$_2$ (Tyr(SO$_3$H) in the amino acid sequence represented by SEQ ID NO: 1 is O-sulfonated tyrosine or a salt thereof; the same shall apply hereinafter.)

(2) a peptide consisting of an amino acid sequence in which one or more amino acids are deleted, substituted or inserted in the amino acid sequence of (1) as mentioned above and has CCK2R agonist activity.

The aforementioned cholecystokinin 2 receptor agonist is absorbed through the skin upon administrating transdermally and exhibits the suppressive effect of itch and may have fewer side effects than steroid drugs for external use or tacrolimus drugs for external use.

In this context, the cholecystokinin 2 receptor agonist is preferably a peptide having the amino acid sequence represented by SEQ ID NO: 2 shown below and/or a peptide having the amino acid sequence represented by SEQ ID NO: 3 shown below.

[SEQ: ID No. 2]
Asp-Tyr(SO$_3$H)-Met-Gly-Trp-Met-Asp-Phe-NH$_2$

[SEQ: ID No. 3]
Tyr(SO$_3$H)-Met-Gly-Trp-Met-Asp-Phe-NH$_2$

The itch suppressant according to the present invention may suppress the degranulation of mast cells. Because of this, onset of itch and inflammation response mediated by signaling by mast cells may be suppressed.

The itch suppressant according to the present invention may be in the form of injections, ointments, creams, liquids for external use, sprays, plasters or gels.

These formulations are suitable to local subcutaneous or transdermal administration.

Effects of the Invention

The present invention provides a novel itch suppressant effective in treating skin illnesses associated with strong itch such as atopic dermatitis having few side effects.

EMBODIMENTS OF THE INVENTION

The itch suppressant according to an embodiment of the present invention comprises cholecystokinin 2 receptor (CCK2R) agonist as an active ingredient. As the CCK2R agonist for the production of the itch suppressant, any substances that bind to the CCK2R of which expression is selectively enhanced by itch-inducing substance and exhibit the physiology associated with the suppression of itch may be used. Examples of the CCK2R agonists include some peptides belonging to CCK family and their analogues and the suitable substance may be selected depending on the administration route, the kind of skin illness to be treated and the like. Particular examples include (1) a peptide having the total amino acid sequence of cholecystokinin containing C-terminal or a peptide containing an amino acid sequence homologous with a partial amino acid sequence of at least three C-terminal amino acids of its amino acid sequence or (2) a peptide consisting of an amino acid sequence in which one or more amino acids are deleted, substituted or inserted in the amino acid sequence of (1) as mentioned above and has CCK2R agonist activity (hereinafter may be collectively referred to as "cholecystokinin peptide"). Among these peptides, only one or any two or more peptides having different amino acid chain length may be used for the production of the itch suppressant.

The molecular weight of the cholecystokinin peptide used is selected depending on the agonist activity to CCK2R, administration route and the like. In general, the upper limit of the molecular weight of the substance that may be absorbed transdermally is about 3000, however, the substances having the molecular weight of more than 3000 may also be absorbed transdermally in case that keratinous layer is damaged due to the skin illness and the like. Therefore, the molecular weight of the cholecystokinin peptides used for the production of the itch suppressant for transdermal administration is not necessary to be 3000 or less. Thus the CCK2R agonist is preferably applicable to the production of the itch suppressant includes:

(1) a peptide having an amino acid sequence homologous with a partial amino acid sequence of at least seven C-terminal amino acids of the peptide having the amino acid sequence represented by SEQ ID NO: 1; and

```
                                           [SEQ: ID No. 1]
Val-Ser-Gln-Arg-Thr-Asp-Gly-Glu-Ser-Arg-Ala-His-

Leu-Gly-Ala-Leu-Leu-Ala-Arg-Tyr-Ile-Gln-Gln-Ala-

Arg-Lys-Ala-Pro-Ser-Gly-Arg-Met-Ser-Ile-Val-Lys-

Asn-Leu-Gln-Asn-Leu-Asp-Pro-Ser-His-Arg-Ile-Ser-

Asp-Arg-Asp-Tyr(SO₃H)-Met-Gly-Trp-Met-Asp-Phe-NH₂
```

(2) a peptide consisting of an amino acid sequence in which one or more amino acids are deleted, substituted or inserted in the amino acid sequence of (1) as mentioned above and has CCK2R agonist activity.

Examples of the substitution of amino acid include the substitution of O-sulfonated tyrosine located at the seventh position from C-terminal in the amino acid sequence represented by SEQ ID NO: 1 with normal tyrosine, substitution of the amidated phenylalanine at the C-terminal with normal (nonamidated) phenylalanine and the like.

These peptides may be used alone or in combination of any two or more for the production of the itch suppressant.

Examples of more preferable cholecystokinin peptide include a peptide having the amino acid sequence represented by SEQ ID NO: 2 shown below or a peptide having the amino acid sequence represented by SEQ ID NO: 3 shown below.

```
                                           [SEQ: ID No. 2]
Asp-Tyr(SO₃H)-Met-Gly-Trp-Met-Asp-Phe-NH₂

[SEQ: ID No. 3]
Tyr(SO₃H)-Met-Gly-Trp-Met-Asp-Phe-NH₂
```

These peptides may be used alone or in combination of any two or more for the production of the itch suppressant.

The origin of these cholecystokinin peptides are not particularly limited and any of the peptide from biological source, produced by microorganisms such as *E. coli* using gene recombination and synthesized chemically may be use.

The itch suppressant is produced by mixing the CCK2R agonist such as aforementioned cholecystokinin peptides with pharmaceutically acceptable additives in defined ratios. The itch suppressant may be formulated in any dosage forms suitable for local subcutaneous or transdermal administration.

Examples of the dosage forms include liquid formulations for external use such as an injection, an ointment, a cream, a gel, a spirit, a liniment and a lotion; plasters such as a spray (an aerosol for external use), a tape, a cataplasm.

In the transdermal administration, at least a part of keratinous layer may be removed by tape stripping and the like to enhance the absorption rate of CCK2R agonist.

Type and amount of the additives used is selected depending on the dosage forms, kind of CCK2R used as the active ingredient (structure, molecular weight and the like). Particular examples of the additives include as follows:

(a) injections: aqueous solvents such as injection solvent, physiological saline and Ringer's solution; non-aqueous solvents such as vegetable oil; surfactants or emulsifier (in case of suspensions or emulsions).

(b) ointments: hydrophobic bases such as petrolatum, paraffin, Plastibase®, silicone, beeswax and oil extracted from animals and plants; hydrophilic bases such as hydrophilic ointment, hydrophilic petrolatum, purified lanolin and macrogol.

(c) lotions: solvents such as ethanol and glycerol; suspending agents such as gum arabic, sodium arginate and methylcellulose; emulsifiers such as sodium laurylsulfate, polysorbic acid esters.

(d) aerosols for external use: liquid gases such as LPG, dimethyl ether, fluorocarbons; compressed gasses such as nitrogen, carbon dioxide; solvents, suspending agents and emulsifiers (in case of emulsion type).

In addition, other additives such as stabilizing agents, sanitizing agents, preserving agents and fragrances may be added as needed. Also, the itch suppressant may be used in combination with other medicines for treating skin illnesses.

The amount of CCK2R agonist added in these formulations as active ingredient may be determined depending on the usage and the dose of the formulation. For example, in case of liquid formulations, the formulation is prepared so that it contains 0.1 to 0.5 nmol/13 µL (the amount of the liquid formulation required for applying on 1 cm² of skin) more preferably 0.2 to 0.35 nmol/13 µL of CCK2R agonist. It is difficult to determine the amount of administered CCK2R agonist unambiguously since it depends on the factors such as kind of the compound, administration route, conditions and age of patient, for example, 0.1 to 0.5 nmol/cm², preferably 0.2 to 0.35 nmol/cm².

EXAMPLES

Hereinafter, examples carried out for confirming the effect of the present invention is described.

[1] Materials and Experimental Animals

The cholecystokinin peptides used for the example is five peptides having the amino acid sequences represented by SEQ ID NOS: 2 to 6 shown below.

```
CCK8S
                                           [SEQ: ID No. 2]
Asp-Tyr(SO₃H)-Met-Gly-Trp-Met-Asp-Phe-NH₂

CCK7S
                                           [SEQ: ID No. 3]
Tyr(SO₃H)-Met-Gly-Trp-Met-Asp-Phe-NH₂

CCK8
                                           [SEQ: ID No. 4]
Asp-Tyr-Met-Gly-Trp-Met-Asp-Phe-NH₂

CCK7
                                           [SEQ: ID No. 5]
Tyr-Met-Gly-Trp-Met-Asp-Phe-NH2

CCK6
                                           [SEQ: ID No. 6]
Met-Gly-Trp-Met-Asp-Phe-NH₂
```

Herein, the term "CCKmS" (m is 7 or 8) referred to "natural type" cholecystokinin in which the tyrosine located at seventh position from C-terminal is sulfated and the term "CCKn" (n is 6, 7 or 8) referred to cholecystokinin analogues in which the tyrosine located at seventh position from C-terminal is not sulfated. CCK8S, CCK8, CCK7S and CCK6 were purchased from Peptide Institute, Inc. (Osaka, Japan) and CCK7 was purchased from Funakoshi Corporation (Tokyo, Japan).

Substance P (SP) was purchased from Peptide Institute (Osaka, Japan). Compound 48/80, a test substance that stimulates mast cells to cause degranulation was purchased from Sigma (St. Louis, Mo.). Histamine was purchased from Wako Pure Chemicals (Osaka, Japan). Protease-activated receptor-2 (PAR-2) and hexapeptide Ser-Leu-Ile-Gly-Arg-Leu-$NH_2$ agonist were purchased from Tocris (Ellisville, Mo.).

Female ICR mice and female C57BL/6J mice were purchased from KBT Oriental Co. (Tosu, Japan). These mice were maintained in the Laboratory Animal Research Center in University of Occupational and Environmental Health under specific pathogen-free (SPF) conditions, and used at age of 6-8 weeks.

All animal experiments were performed according to the guidelines for the care and use of animals approved by University of Occupational and Environmental Health, Japan.

Cells and Cell Culture

1) Normal Human Epidermal Keratinocytes (NHEKs)

Primary culture of normal human epidermal keratinocytes (NHEKs) was purchased from Lonza (Basel, Switzerland). NHEKs were grown in Keratinocyte Growth Medium-2 (KGM-2; Lonza) and used for experiments in Keratinocyte Basal Medium-2 (KBM-2; Lonza). Both of the cultivation and the experiments were carried out in an incubator at 37° C. in a 5% $CO_2$ atmosphere.

2) Keratinocytes Derived from ICR Mouse

The skin of ICR newborn mouse was peeled within 24 hours after birth and incubated with 0.05% collagenase (collagenase from *Clostridium histolyticum* type 2; Sigma) for 2 days at 37° C. in a 5% $CO_2$ atmosphere. Epidermal sheets were collected and suspended in culture medium. Cell suspension was plated into six-well plates (Corning Glass Works, Corning, N.J.) and grown to subconfluence in CnT-07 medium (Funakoshi).

3) Mouse Fetal Skin Derived Mast Cells (FSMCs)

Day 14 mouse fetal skin was dissociated by trypsin for 20 min at 37° C. in Hank's balanced salt solution (HBSS; Gibco, Carlsbad, Calif.). Erythrocytes were lyzed using RBC lysing buffer (Sigma) and, after washing, cells were resuspended in complete RPMI, which is RPMI-1640 (Gibco) supplemented with 5% fetal bovine serum (FBS; Gibco), 1% nonessential amino acids (Gibco), 1% sodium pyrubate (Gibco), antibiotic/anti-mycotic (Invitrogen, Carlsbad, Calif.), and 0.1% 2-mercaptoethanol (Gibco). Fifty mL of the cell suspension in each flask (Corning, Corning, N.Y.) was cultured in the presence of 20 ng/mL recombinant mouse IL-3 (Invitrogen) and 20 ng/mL recombinant mouse stem cell factor (Biosource, Camarillo, Calif.) at 37° C. without changing the medium. Nonadherent and loosely adherent cells were harvested. The cells were centrifuged and resuspended in RPMI, and layered on 40% Percoll (GE Healthcare, Buckinghamshire, England), and centrifuged at room temperature. The cell-pellet at the bottom was used as FSMCs.

4) Rat Pheochromocytoma Cell Line (PC12)

PC12 (JCRB0733) was obtained by Health Science Research Resources Bank (Tokyo, Japan). PC12 cells were cultured in Dulbecco's Modified Eagle Medium (DMEM; Sigma) supplemented with 10% FBS. For experiment, PC12 cells were plated on fibronectin-coated coverslips, and they were used after treatment of recombinant rat β-NGF at least for 24 hours.

[2] Analysis

Statistical Analysis

Data were analyzed using an unpaired Student's t-test. $P<0.05$ was considered to be significant.

Microarray

For DNA microarray analysis, total RNA was extracted from NHEKs with the RNeasy Mini Kit (QIAGEN, Valencia, Calif.). Images obtained from a plate reader were analyzed with DNASIS Array (DNA CHIP RESERCH Inc., Hitachi Software Engineering, Tokyo, Japan), according to the manufacturer's instructions.

Real-Time Quantitative RT-PCR Analysis

Total RNA was extracted with PureLink RNA Mini Kit (Invitrogen) from cell-pellet. cDNA was reverse transcribed from total RNA samples using the TAQMAN (Reverse Transcription reagents) (Applied Biosystems, Carlsbad, Calif.). mRNA expression was quantified by real-time PCR using SYBR Green Dye (PE Biosystems, Foster City, Calif.) with ABI PRISM 7000 Sequence Detection System (Applied Biosystems) according to the manufacturer's instructions. Primers were designed using Primer Bank for human and murine gene and Primer 3 for rat gene, and they were constructed by Invitrogen. The primer sequences (Invtrogen) are as follows:

```
human β-actin:
GGGAAATCGTGCGTGACATT
and

GGAGTTGAAGGTAGTTTCGTG, human CCK2R:
GGGACACGAGAATTGGAGCTG
and

CGGTGCCAAAGATGAATGTGC, human NK1R:
CTCAGACCTCTCCCCAAACAT
and

CCACAATGACCGTGTAGGCAG, mouse β-actin:
GGGAAATCGTGCGTGACATT
and

GGAGTTGAAGGTAGTTTCGTG, mouse CCK2R:
GATGGCTGCTACGTGCAACT
and

CGCACCACCCGCTTCTTAG, mouse CCK1R:
CACGCTGGTTATCACGGTG
and

GCCCATGAAGTAGGTGGTAGTC mouse NK1R:
CTCCACCAACACTTCTGAGTC
and

TCACCACTGTATTGAATGCAGC, rat β-actin:
AGCCATGTACGTAGCCATCC
and

CTCTCAGCTGTGGTTGGTGAA, rat CCK2R:
TCTCCCGCGAACTCTACCTA
and
```

-continued

ACACAGCAGCCATCACTGTC, rat NK1R:
TGGGCAACGTAGTGGTGATA
and

CACGGCTGTCATGGAGTAGA.

The conditions of the real-time PCR were as follows: 2.0 min at 50° C., 10 min at 95° C., and then 50 cycles of amplification consisting of 15 sec at 95° C. and 1 min at 60° C.

All heating and cooling steps were performed with a slope of 20° C./min. The relative expression was calculated using the Δ Ct method.

Western Blotting

Keratinocytes from ICR mice were stimulated with SP ($10^{-8}$ M) in six-well plates (Corning Glass Works) for 0.5-24 hours, harvested with a rubber policeman, and subjected to extraction with RIPA buffer (Wako, Osaka, Japan; Tris-HCl (pH 8.0), 150 mM sodium chloride, 0.5% (wt/vol) sodium deoxycholate, 0.1% (wt/vol) SDS, and 1.0% (wt/vol) NP-40 substitute). Protein samples (20 μg) were separated by 8% SDS-polyacrylamide gel electrophoresis and electroblotted onto polyvinylidene difluoride membranes for 2 hours at 180 mA. After blocking with skim milk solution, the membranes were incubated with rabbit anti-mouse CCK1R(SC-33220; 1:1,000, Santa Cruz, Santa Cruz, Calif.) polyclonal antibodies, or CCK2R(SC-33221; 1:1,000, Santa Cruz) polyclonal antibodies, and the reaction was detected with horseradish peroxidase-conjugated goat anti-rabbit IgG (1:3,000, Bio-Rad, Hercules, Calif.). Immunoblots were visualized using the ECL Plus Western Blotting Detection Reagents (GE Healthcare) according to the manufacturer's protocol. Bands were quantified by densitometry with the help of a CS Analyzer version 2.0 (ATTO, Tokyo, Japan). NIH/3T3 whole cell lysate (Santa Cruz) was used as a positive control.

Cytometric Beads Array

IL-8 concentration in the culture supernatants was quantified with Cytometric Bead Array (CBA) Flex Set System purchased from BD using FACSCanto (BD).

Flow Cytometry

Cells were stained with Phycoerythrin (PE)-conjugated anti-mouse FcεRI (eBioscience, San Diego, Calif.) and Alexa Fluor 700-conjugated anti-mouse CD117 (cKit) (eBioscience) for 20 min on ice, washed twice and then resuspended with FACS buffer. Flow cytometric analysis was performed with FACSCanto (BD) and FlowJo software (TreeStar, San Carlos, Calif.).

(1) CCK2R Expression in Keratinocytes and Mast Cells

Both keratinocytes and mast cells are the possible targets of CCKs in the suppression of SP-induced pruritus. It is known that keratinocytes express the receptors for itch-related molecules, as represented by NK1R for SP, H1 receptor for histamine, and protease-activated receptor-2 (PAR-2) for tryptase (synthetic agonist, SLIGRL-$NH_2$). Mast cells are well known to possess NK1R.

We investigated the expression of CCK receptors, CCK1R and CCK2R, in keratinocytes derived from ICR mouse and mouse fetal skins derived mast cells (FSMCs). In parallel, the expression of NK1R was also monitored. Primary cultures of keratinocytes from ICR mice and FMSCs were collected, and mRNAs for CCK1R, CCK2R and NK1R were semiquantitated by real-time PCR analysis.

Figure 1:
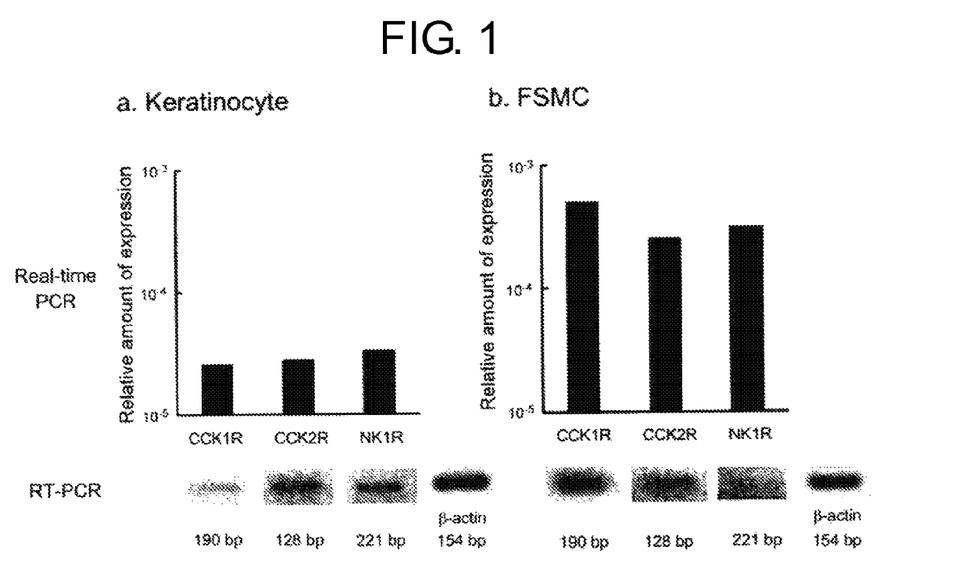
FIG. 1 shows a graph showing expression levels of CCK1R, CCK2R and NK1R in keratinocytes from ICR mice and murine fatal skin-derived cultured mast cells (FSMC).

As shown in FIG. 1, in the two types of cells, both CCK1R and CCK2R were expressed at comparable levels to NK1R. When the expression levels were normalized with the β-actin level, the three receptors were more highly expressed in FSMCs (FIG. 1b) than keratinocytes (FIG. 1a).

(2) SP-Induced Expression of CCK2R in Normal Human Keratinocytes (NHEKs)

It is known that keratinocytes express the receptors for itch-related molecules such as NK1 receptor (SP), H1 receptor (histamine), and PAR-2 (tryptase, synthetic agonist, SLI-GRL-$NH_2$ (Ser-Leu-Ile-Gly-Arg-Leu-$NH_2$)) (agonist for each receptor is shown in parenthesis).

In a preliminary analysis of normal human keratinocytes (NHEKs) using DNA microarray method, we investigated the gene expression level when they were stimulated with SP ($10^{-6}$ M), histamine (10 μM/mL) or SLIGRL-$NH_2$ (100 nM) under high calcium concentration (0.6 mM).

Table 1 shows the top 20 genes whose expression levels were prompted by the stimulation with SP together with the values observed for histamine and SLIGRL-$NH_2$ stimulated NHEKs. The values are log 2 (mRNA expression level of each stimulated sample/expression level of the control). Normal human keratinocytes were cultivated with substance P ($10^{-6}$ M), histamine (10 μM/mL) and SLIGRL-$NH_2$ (100 nM) and the mRNA expression ratios ($2^n$) were calculated by comparing with non-stimulated normal human keratinocytes. Microarray analysis of the expression levels of mRNA showed that CCK2R was highly expressed in NHEK stimulated with SP and its expression ratio was $2^{8.67}$. However, no significant changes were observed in the expression levels of CCK2R in NHEKs stimulated with histamine and SLIGRL-$NH_2$. These results suggest that CCK2R was selectively upregulated by SP.

Table 1. Top 20 mRNAs Highly Expressed in Normal Human Keratinocytes Stimulated

TABLE 1

Top 20 mRNAs highly expressed in normal human keratinocytes stimulated with SP

| Gene Names | Accession ID | SP | histamine | SLIGRL |
|---|---|---|---|---|
| CCK2R | NM_176875 | 8.67 | −0.01 | 0.06 |
| FCN3 | NM_173452, NM_003665 | 4.50 | −0.23 | −0.62 |
| PTN | NM_002825 | 4.04 | −0.14 | 0.12 |
| ANKRD6 | NM_014942 | 3.20 | 0.00 | −0.17 |
| BUB1B | NM_001211 | 3.06 | −1.09 | 0.52 |
| RASSF7 | NM_003475 | 1.82 | | |
| F10 | NM_000504 | 1.74 | 1.36 | |
| CKM | NM_001824 | 1.72 | 1.04 | |
| ARG1 | NM_000045 | 1.69 | | 0.71 |
| SV2B | NM_014848 | 1.54 | | |
| CYP17A1 | NM_000102 | 1.40 | 1.14 | 0.92 |
| CLEC7A | NM_197950, NM_197954, NM_197948, NM_022570, NM_197947, NM_197949 | 1.16 | | |
| ICAM1 | NM_000201 | 1.16 | | |
| MMP9 | NM_004994 | 1.12 | 4.02 | 0.11 |
| MAP3K1 | XM_001128827, XM_042066 | 1.06 | 0.88 | 0.64 |
| PDE7B | NM_018945 | 1.02 | 0.12 | 1.00 |
| SERPINI2 | NM_006217 | 1.00 | 0.38 | 0.72 |
| NDRG4 | NM_020465, NM_022910 | 1.00 | 1.59 | |
| AR | NM_000044, NM_001011645 | 0.99 | | |
| ACTL7B | NM_006686 | 0.99 | 0.63 | 0.84 |

(3) SP-Induced Expression of CCK2R in ICR Mouse Keratinocytes

To determine the effect of SP on keratinocytes, ICR mouse keratinocytes were incubated with SP for 30 min to 24 hours and the expression of CCK2R and CCK1R were analyzed by western blotting. CCK2R was detected with antibodies as 78 kDa band, and increased in keratinocytes exposed to SP for 5 or 6 hours. On the other hand, CCK1R expression was not augmented by SP.

(4) Effects of CCKs on SP-Induced Scratch Behavior

Since it is considered that external administration of CCK affects keratinocytes, at first, CCK2R agonist was administered transdermally (applying the solution prepared using acetone-olive (3:1)) to itch-related behavior model (ICR mice administered intradermally with SP (100 nmol)).

The hair was clipped over the rostral part of the murine back one or two days prior to experiment. Before behavioral recording, each mouse (4 animals per observation) was put into an acrylic cage (18×23×11 cm) for at least 1 hr for acclimation. An intradermal injection of SP (100 nmol in normal saline per site) induces scratching of the skin around the injected site by the hind paws in mice. CCKs were topically applied in the two ways, percutaenous application and intradermal injection. For percutaneous application, the shaved back skin was stripped with SCOTCH brand tape (3M) 6 times the day before the experiment. The mice were painted on the clipped back with 204 CCK (0.5 nmol/site) in acetone/olive (3:1) 3-4 minutes before SP injection (100 nmol/site). For intradermal injection, mice were injected intradermally with CCK (0.5 nmol/site in 20 µl normal saline) simultaneously with SP. Immediately after treatment, the animals were put back into the same cage and their behavior was videotaped using a digital video camera for 40 minutes. The frequency of scratch toward the injected site by hind paws was counted for the first 20 minutes with the video.

Figure 2A:
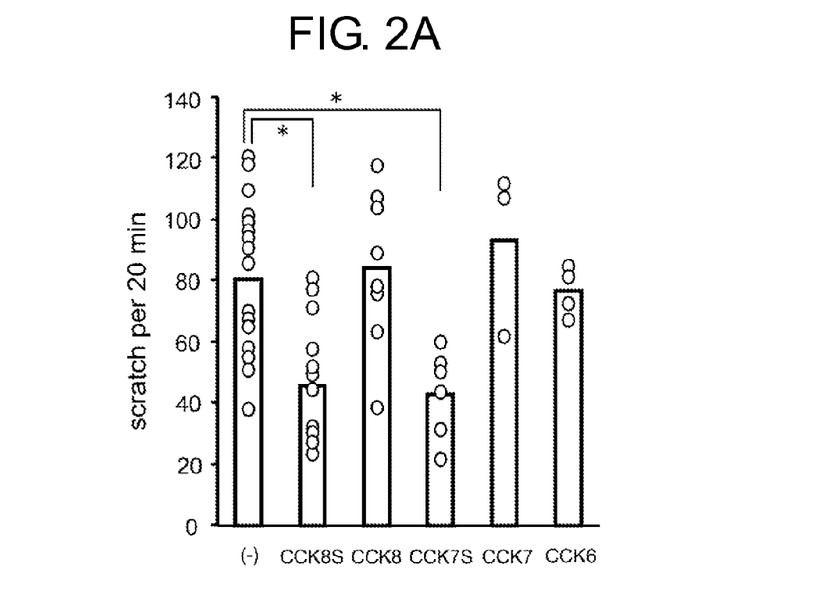
FIG. 2A shows a graph showing the influence of transdermal administration of CCK2R agonist on the scratch behavior in ICR mice induced the itch by the stimulus of substance P (SP).

As shown in FIG. 2, in the animals administered with CCK8S and CCK7S significant reduction in the scratch behavior was observed. On the other hand, in the animals administered with CCK8, CCK7, and CCK6 no significant reduction in the scratch behavior was observed.

These results suggest that at least 7 amino acid of CCK at sulfated amino acid (tyrosine) located at seventh position from C-terminal was indispensable for the ability to depress the scratch behavior.

Figure 2B:
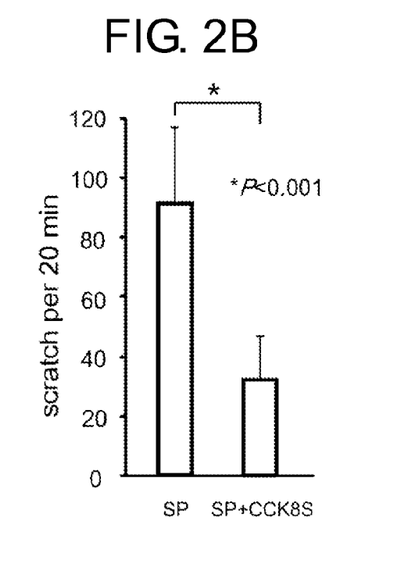
FIG. 2B shows a graph showing the influence of subcutaneous administration of CCK8S on the scratch behavior in ICR mice induced the itch by the stimulus of SP.

In addition, the scratch behavior was also depressed by the subcuteneous administration of CCK8S. These results suggest that dermal cells involving the development of itch, such as mast cells, are also the target of CCK as well as keratinocytes.

(5) CCK2R Expression in Mast Cells and Neuronal Cells (Cell Cultures)

Based on the fact that NK1 receptor (NK1R) is expressed in mast cells, and the aforementioned experimental result that intradermal CCK8S injection depressed SP-induced itch, we clarified whether mast cells and neuronal cells express CCK2R and NK1R, along with keratinocytes.

Figure 3:
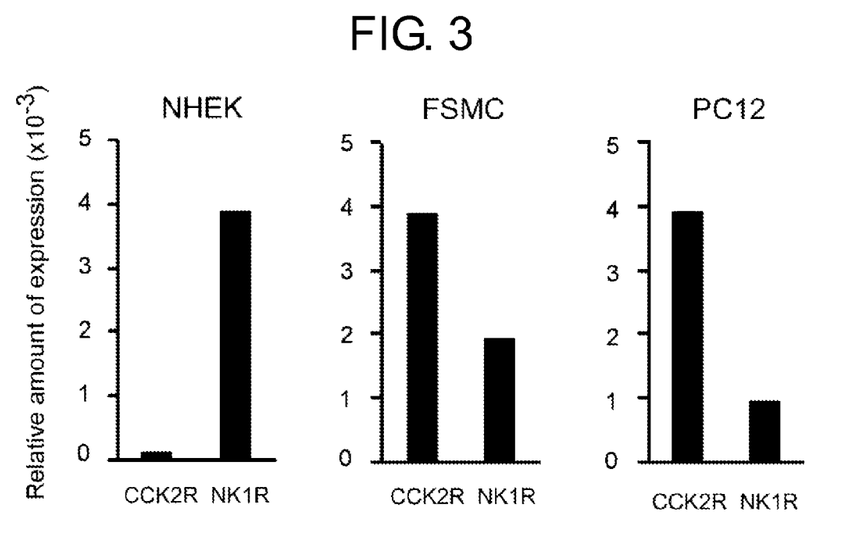
FIG. 3 shows a graph showing the expression levels of CCK2R and NK1R in human epidermal keratinocytes (NHEK), FSMC and rat adrenal pheochromocytoma cells (PC12).

NHEK, FSMC (mouse fetal skin derived mast cells) and PC12 (rat pheochromocytoma cell) were selected as representative keratinocytes, mast cells, and neuronal cell, respectively and cell cultures of these cells were collected, and mRNAs for CCK2R and NK1R were estimated by real-time PCR analysis. As shown in FIG. 3, it was confirmed that both CCK2R and NK1R were expressed in the three types of cells, and CCK2R was expressed in NHEKs to a lesser degree than those of in FSMC and PC12.

(6) Effect of Administration of CCK2R Agonist on IL-8 Production in Keratinocyte and Degranulation in Mast Cell The results as described above suggest that CCK8S suppresses the itch by depressing the activities of keratinocytes and mast cells. To clarify the target cell of CCK8S associated with the suppression of the itch, the effects of the administration of CCK8S in keratinocytes and mast cells were investigated in vitro.

Figure 4A:
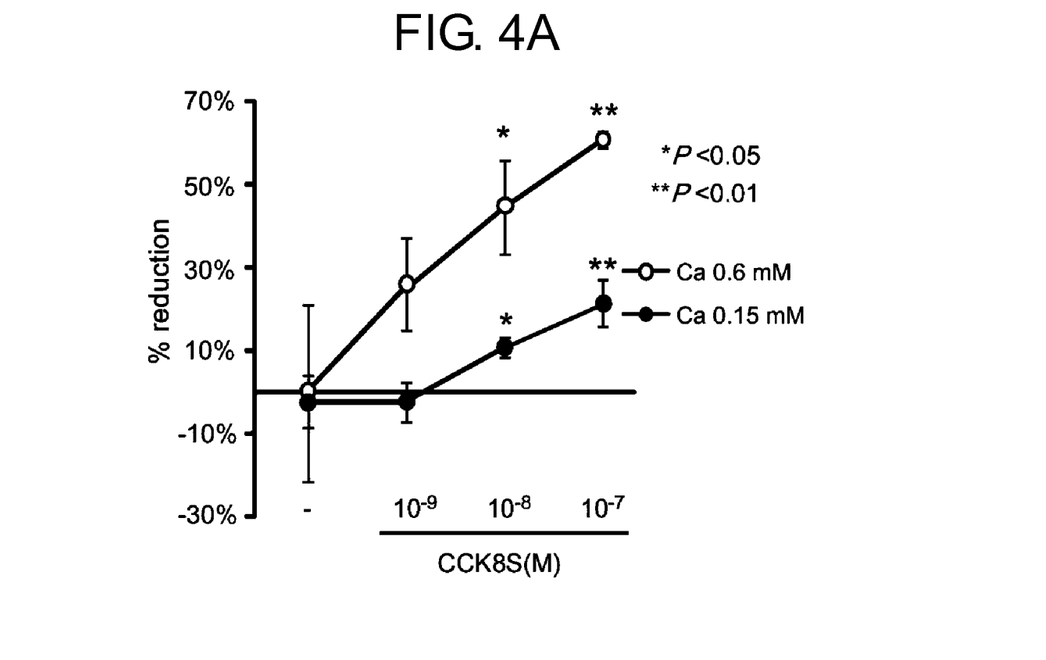
FIG. 4A shows a graph showing the relationship between the administration concentration of CCK8S and the reduction rate of IL-8 production in NHEK.

NHEKs were stimulated with various concentrations of CCK8S (CCK8S concentration of $10^{-9}$, $10^{-8}$, or $10^{-7}$ M, Ca concentration of 0.15 mM or 0.6 mM). As a result, the production of IL-8 decreased in accordance with the concentration of CCK8S under any Ca concentrations (see FIG. 4A).

β-Hexosaminidase Assay

FSMCs were washed with Tyrode's buffer (Sigma), and resuspended at 2×10$^4$ cells per well into a 96 well plate. FSMCs were treated with compound 48/80 with or without CCK8S for 15 min at 37° C. The plate was centrifuged for 5 min and supernatant was placed into another 96 well and cell pellet were resuspended with 0.5% Triton X-100 (Sigma) in Tyrode's buffer. Supernatant and cell lysate (50 µl) was incubated with 100 µl 4 mM p-nitrophenyl-N-acetyl-β-D-galactosaminide (Sigma), dissolved in citrate buffer, pH4.5, at 37° C. for 90 min. The reaction is stopped with 200 µl 0.2M Glycine (MP Biomedicals, Solon, Ohio), pH10.7. The plate was read at 405 nm using a reference filter 595 nm by Microplate Reader (Bio-Rad, Hercules, Calif.). β-hexosaminidase release was determined as the ratio between activity in the supernatant and cell lysate multiplied by 100.

Figure 4B:
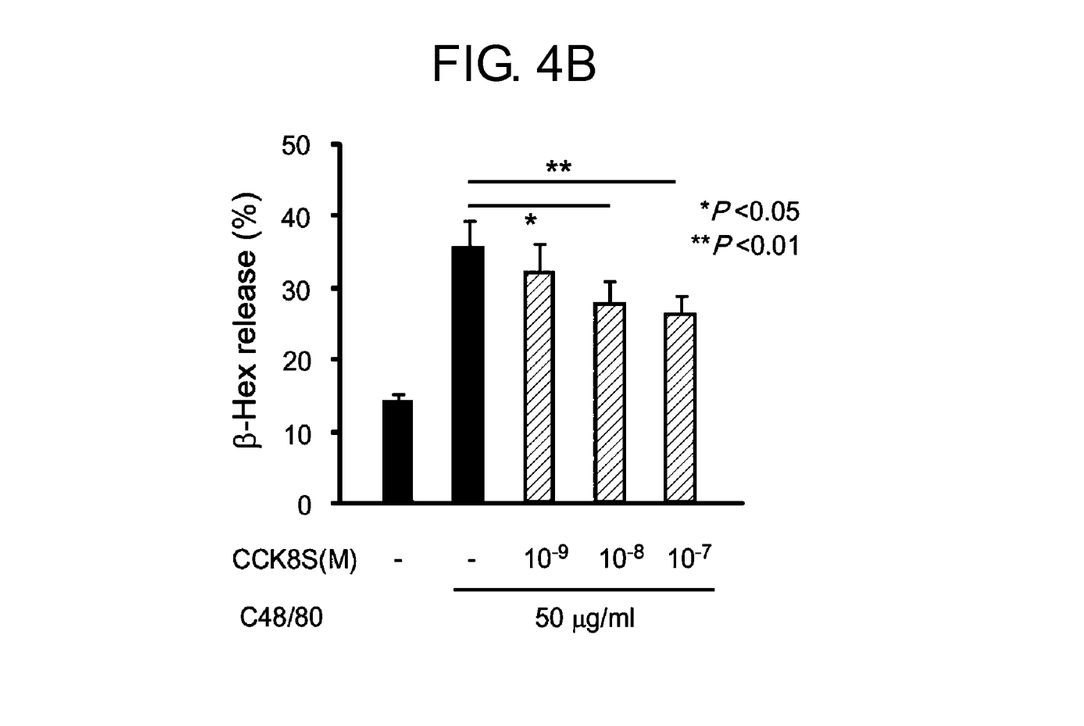
FIG. 4B show a graph showing the relationship between the administration concentration of CCK8S and the reduction rate of degranulation of FSMC.

The addition of compound 48/80 induces degranulation in FSMCs. Upon adding CCK8S (at $10^{-8}$ or $10^{-7}$M), the suppression of degranulation was observed (see FIG. 4B). The result suggests that CCK8S suppresses the mast cell functions.

(7) Effect of the Administration of CCK2R Agonist on Contact Hypersensitivity Mouse Model Effect of the administration of CCK8S was also investigated using a contact hypersensitivity (CHS) mouse to DNFB.

Sensitization and Challenge of CHS and Administration of Cholecystokinin Peptides For induction of CHS to 2,4-dinitrofluorobenzene (DNFB; Nakalai Tesque, Kyoto, Japan), ICR mice were sensitized on two consecutive days, days 0 and 1, on the clipped abdomen with 25 µL of 0.5% of DNFB diluted in acetone/olive oil (3:1). Five days later, animals were challenged on both sides of each ear by painting a nonirritant concentration of 0.2% DNFB. Before challenge, CCK8S (0.5 nmol/ear) diluted in acetone/olive oil (3:1) or only acetone/olive oil (control) was painted on each ear. The ear thickness of mice was measured using dial thickness gauge before and 24 hours after challenge. Ear swelling was calculated from the difference in ear thickness between before and after challenge.

Figure 4C:
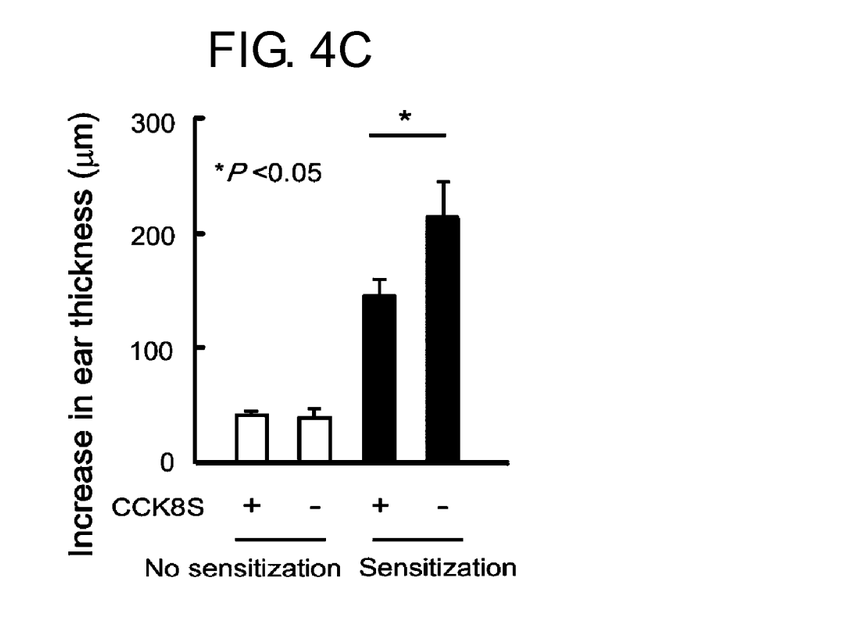
FIG. 4C shows a graph showing the relationship between the presence or absence of challenge and the administration of CCK8S and the thickness of pinna of ear in CHS model mice.

In CHS model, mice were sensitized with DNFB (2,4-dinitrofluorobenzene), a haptene, and the contact hypersensitivity raised by DNFB at day 5 lead to ear swelling. As shown in FIG. 4C, when CCK8S was administered immediately before the challenge the ear swelling was suppressed.

Component cells of skin such as keratinocytes, dendritic cells and mast cells involve CHS elicitation phase and it was suggested that CCK8S suppressed these cells. From these results, it was predicted that CCK8S affected keratinocytes and mast cells to suppress the CHS. It is considered that CCK8S suppresses the production of chemokine and cytokine and immune response in addition to the direct suppression of itch-related responses.

(8) Change of Ca Influx by CCK8S

Since the application of CCK8S immediately exerted its inhibitory effects on the scratch behavior, a possibility was raised that CCK8S directly affect peripheral nerve as well as mast cells. To test whether CCK8S affects mast cells or neuronal cells, we measured the intracellular Ca using confocal microscope.

Confocal Imaging

Confocal imaging of cells loaded with fluorescent dyes was undertaken using a Zeiss LSM5 pascal (Carl Zeiss, Jena, Germany). Fluo-4-AM (Invitrogen) (1 µM) was loaded at 37° C. for 20 min and washed twice and sit at least for 40 min. Mast cells, were stained for CD117 (c-kit) with Alexa Fluor 700-conjugated anti-mouse CD117 antibody. The LSM5 multi-track configuration was used for simultaneous measurement of intracellular Ca concentration (Ca) (excitation, 488 nm; emission, long-pass 505 nm filter) and the expression of CD117 (excitation, 633 nm; emission, long-pass 650 nm filter). Images were recorded at room temperature with 512× 512 pixels. The application of stimulation, such SP and CCK, were applied directly in the bath as a small drop (10 µL). Image data were analyzed off-line using the Zeiss LSM510 analyzing software (LSM Image Examiner).

Figure 5:
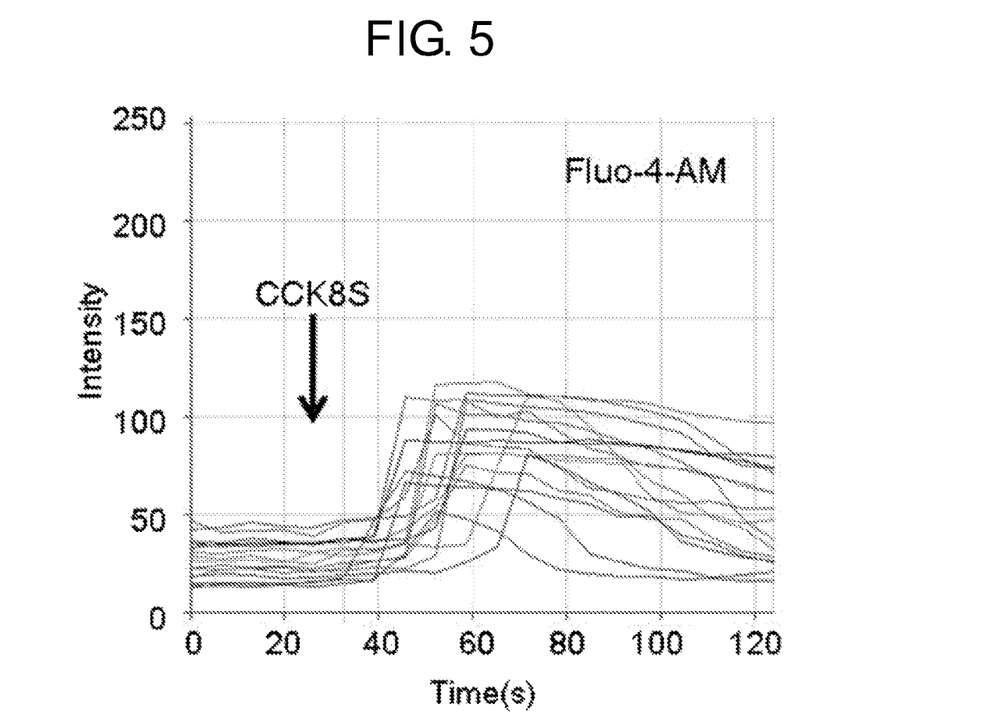
FIG. 5 shows a graph showing the change of intracellular Ca concentration in FSMC after the administration of CCK8S.

As shown in the graph on the top of FIG. 5, the administration of CCK8S on FSMCs induced a transient increase in Ca within 1 minute after the administration, and the percentage of responding FSMCs was determined to be 45%, as shown in the graph on the bottom of FIG. 6. Thus, it is likely that CCK8S affects signaling in mast cells.

INDUSTRIAL APPLICABILITY

The present invention may be applicable to the itch suppressant associated with itch such as atopic dermatitis.

The invention claimed is:

1. A method of suppressing itching comprising subcutaneous or transdermal administration of an effective amount of an itch suppressant containing cholecystokinin 2 receptor (CCK2R) agonist as an active ingredient, wherein the itch suppressant suppresses degranulation of mast cells, to a patient in need thereof.

2. A method of suppressing itching comprising subcutaneous or transdermal administration of an effective amount of a cholecystokinin 2 receptor agonist, wherein the cholecystokinin 2 receptor agonist is one or more peptides having an amino acid sequence of at least amino acids 52-58 of SEQ ID NO:1;

[SEQ: ID No. 1]
Val-Ser-Gln-Arg-Thr-Asp-Gly-Glu-Ser-Arg-Ala-His-

Leu-Gly-Ala-Leu-Leu-Ala-Arg-Tyr-Ile-Gln-Gln-Ala-

Arg-Lys-Ala-Pro-Ser-Gly-Arg-Met-Ser-Ile-Val-Lys-

Asn-Leu-Gln-Asn-Leu-Asp-Pro-Ser-His-Arg-Ile-Ser-

Asp-Arg-Asp-Tyr(SO₃H)-Met-Gly-Trp-Met-Asp-Phe-NH₂

Wherein Tyr(SO₃H) is -sulfonated tyrosine or a salt thereof.

3. A method of suppressing itching comprising subcutaneous or transdermal administration of an effective amount of an itch suppressant containing a cholecystokinin 2 receptor agonist, wherein the cholecystokinin receptor 2 agonist is a peptide having the amino acid sequence represented by SEQ ID NO:2 and/or a peptide having the amino acid sequence represented by SEQ ID NO:3;

[SEQ: ID No. 2]
Asp-Tyr(SO₃H)-Met-Gly-Trp-Met-Asp-Phe-NH2

[SEQ: ID No. 3]
Tyr(SO₃H)-Met-Gly-Trp-Met-Asp-Phe-NH2

\* \* \* \* \*